(12) United States Patent
Chen et al.

(10) Patent No.: US 8,498,716 B2
(45) Date of Patent: Jul. 30, 2013

(54) EXTERNAL CONTROLLER FOR AN IMPLANTABLE MEDICAL DEVICE SYSTEM WITH COUPLEABLE EXTERNAL CHARGING COIL ASSEMBLY

(75) Inventors: Joey Chen, Valencia, CA (US); Daniel Aghassian, Los Angeles, CA (US); Thomas Warren Stouffer, Chatsworth, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 955 days.

(21) Appl. No.: 11/935,111

(22) Filed: Nov. 5, 2007

(65) Prior Publication Data

US 2009/0118796 A1    May 7, 2009

(51) Int. Cl.
*A61N 1/18* (2006.01)
*A61N 1/04* (2006.01)

(52) U.S. Cl.
USPC ............... 607/61; 607/60; 607/45; 607/33

(58) Field of Classification Search
USPC .................................................. 607/60
See application file for complete search history.

(56) References Cited

U.S. PATENT DOCUMENTS

| | | | |
|---|---|---|---|
| 5,314,457 A | 5/1994 | Jeutter | 607/116 |
| 6,505,077 B1 | 1/2003 | Kast | 607/61 |
| 6,516,227 B1 | 2/2003 | Meadows | 607/46 |
| 6,553,263 B1 | 4/2003 | Meadows | 607/61 |
| 6,658,300 B2 | 12/2003 | Govari | 607/60 |
| 7,200,504 B1 | 4/2007 | Fister | |
| 7,286,880 B2 | 10/2007 | Olson et al. | |
| 2004/0098068 A1* | 5/2004 | Carbunaru et al. | 607/60 |
| 2005/0088357 A1 | 4/2005 | Hess et al. | |
| 2005/0113887 A1 | 5/2005 | Bauhahn | 607/61 |
| 2005/0143781 A1 | 6/2005 | Carbunaru et al. | |
| 2005/0187590 A1* | 8/2005 | Boveja et al. | 607/45 |

(Continued)

FOREIGN PATENT DOCUMENTS

| | | |
|---|---|---|
| JP | 2004-73725 A | 3/2004 |
| WO | 2005/032658 A1 | 4/2005 |
| WO | 20070124325 A | 11/2007 |
| WO | WO 2007124325 A2 * | 11/2007 |

OTHER PUBLICATIONS

U.S. Appl. No. 11/780,369, filed Jul. 19, 2007, Dronov.
U.S. Appl. No. 11/853,624, filed Sep. 11, 2007, Stouffer.

(Continued)

*Primary Examiner* — Carl H Layno
*Assistant Examiner* — Jon Eric C Morales
(74) *Attorney, Agent, or Firm* — Wong, Cabello, Lutsch, Rutherford & Brucculeri, LLP

(57) ABSTRACT

An improved integrated external controller/charger system useable with an implantable medical device is disclosed. The system comprises two main components: an external controller and an external charging coil assembly that is coupleable thereto. When the external charging coil assembly is coupled to the external controller, the system can be used to both send and receive data telemetry to and from the implantable medical device, and to send power to the device. Specifically, the external controller controls data telemetry by energizing at least one coil within the external controller, and the external controller controls power transmission by energizing a charging coil in the external charging coil assembly, which is otherwise devoid of its own control, power, and user interface. The result is a cheaper, simpler, more compact, and more convenient data telemetry and charging solution for the patient having a medical implant.

8 Claims, 5 Drawing Sheets

U.S. PATENT DOCUMENTS

2007/0060967 A1    3/2007   Strother et al.
2007/0060980 A1    3/2007   Strother et al.
2007/0270921 A1*  11/2007   Strother et al. .............. 607/60

OTHER PUBLICATIONS

Medtronic, Inc.'s Restore™ Rechargeable Neurostimulation System, as described in Applicant's Information Disclosure Statement filed herewith.

Advanced Neuromodulation Systems (ANS), Inc. Eon™ Neurostimulation Systems IPG, as described in Applicant's Information Disclosure Statement filed herewith.

International Search Report regarding application No. PCT/US2008/072885 dated Dec. 12, 2008.

Examiner's first report regarding corresponding Australian patent application No. 2008325058, dated Feb. 3, 2011.

* cited by examiner

EXTERNAL CONTROLLER FOR AN IMPLANTABLE MEDICAL DEVICE SYSTEM WITH COUPLEABLE EXTERNAL CHARGING COIL ASSEMBLY

FIELD OF THE INVENTION

The present invention relates to a data telemetry and/or power transfer technique having particular applicability to implantable medical device systems.

BACKGROUND

Implantable stimulation devices are devices that generate and deliver electrical stimuli to body nerves and tissues for the therapy of various biological disorders, such as pacemakers to treat cardiac arrhythmia, defibrillators to treat cardiac fibrillation, cochlear stimulators to treat deafness, retinal stimulators to treat blindness, muscle stimulators to produce coordinated limb movement, spinal cord stimulators to treat chronic pain, cortical and deep brain stimulators to treat motor and psychological disorders, and other neural stimulators to treat urinary incontinence, sleep apnea, shoulder subluxation, etc. The present invention may find applicability in all such applications, although the description that follows will generally focus on the use of the invention within a Spinal Cord Stimulation (SCS) system, such as that disclosed in U.S. Pat. No. 6,516,227, which is incorporated herein by reference in its entirety.

Spinal cord stimulation is a well-accepted clinical method for reducing pain in certain populations of patients. As shown in FIGS. 1A and 1B, a SCS system typically includes an Implantable Pulse Generator (IPG) 100, which includes a biocompatible case 30 formed of titanium for example. The case 30 typically holds the circuitry and power source or battery necessary for the IPG to function, although IPGs can also be powered via external RF energy and without a battery. The IPG 100 is coupled to electrodes 106 via one or more electrode leads (two such leads 102 and 104 are shown), such that the electrodes 106 form an electrode array 110. The electrodes 106 are carried on a flexible body 108, which also houses the individual signal wires 112 and 114 coupled to each electrode. In the illustrated embodiment, there are eight electrodes on lead 102, labeled $E_1$-$E_8$, and eight electrodes on lead 104, labeled $E_9$-$E_{16}$, although the number of leads and electrodes is application specific and therefore can vary.

Portions of an IPG system are shown in FIG. 2 in cross section, and include the IPG 100, an external controller 12, and an external charger 50. The IPG 100 typically includes an electronic substrate assembly 14 including a printed circuit board (PCB) 16, along with various electronic components 20, such as microprocessors, integrated circuits, and capacitors mounted to the PCB 16. Two coils are generally present in the IPG 100: a telemetry coil 13 used to transmit/receive data to/from the external controller 12; and a charging coil 18 for charging or recharging the IPG's power source or battery 26 using the external charger 50. The telemetry coil 13 can be mounted within the header connector 36 as shown.

As just noted, an external controller 12, such as a hand-held programmer or a clinician's programmer, is used to wirelessly send data to and receive data from the IPG 100. For example, the external controller 12 can send programming data to the IPG 100 to set the therapy the IPG 100 will provide to the patient. Also, the external controller 12 can act as a receiver of data from the IPG 100, such as various data reporting on the IPG's status.

The communication of data to and from the external controller 12 occurs via magnetic inductive coupling. When data is to be sent from the external controller 12 to the IPG 100, coil 17 is energized with an alternating current (AC). Such energizing of the coil 17 to transfer data can occur using a Frequency Shift Keying (FSK) protocol for example, such as disclosed in U.S. patent application Ser. No. 11/780,369, filed Jul. 19, 2007, which is incorporated herein by reference in its entirety. Energizing the coil 17 induces an electromagnetic field, which in turn induces a current in the IPG's telemetry coil 13, which current can then be demodulated to recover the original data.

The external charger 50, also typically a hand-held device, is used to wirelessly convey power to the IPG 100 again by magnetic inductive coupling, which power can be used to recharge the IPG's battery 26. The transfer of power from the external charger 50 is enabled by a coil 17'. When power is to be transmitted from the external charger 50 to the IPG 100, coil 17' is likewise energized with an alternating current. The induced current in the charging coil 18 in the IPG 100 can then be rectified to a DC value, and provided to the battery 26 to recharge the battery.

As is well known, inductive transmission of data or power occurs transcutaneously, i.e., through the patient's tissue 25, making it particular useful in a medical implantable device system.

The inventors consider it unfortunate that the typical implantable medical device system 5 requires two external devices: the external controller 12 and the external charger 50. Both are needed by a typical patient at one time or another with good frequency. The external charger 50 is typically needed to recharge the battery 26 in the IPG 100 on a regular basis, as often as every day depending on the stimulation settings. The external controller 12 can also be needed on a daily basis by the patient to adjust the stimulation therapy as needed at a particular time. Therefore, the patient is encumbered by the need to manipulate two completely independent devices. This means the patient must: learn how to use both devices; carry the bulk of both devices (e.g., when traveling); replace the batteries in both devices and/or recharge them as necessary; pay for both devices, etc. In all, the requirement of two independent external devices is considered inconvenient. This disclosure provides embodiments of a solution to mitigate these problems.

DETAILED DESCRIPTION

The description that follows relates to use of the invention within a spinal cord stimulation (SCS) system. However, the invention is not so limited. Rather, the invention may be used with any type of implantable medical device system that could benefit from improved coupling between an external device and the implanted device. For example, the present invention may be used as part of a system employing an implantable sensor, an implantable pump, a pacemaker, a defibrillator, a cochlear stimulator, a retinal stimulator, a stimulator configured to produce coordinated limb movement, a cortical and deep brain stimulator, or in any other neural stimulator configured to treat any of a variety of conditions.

Figure 3:
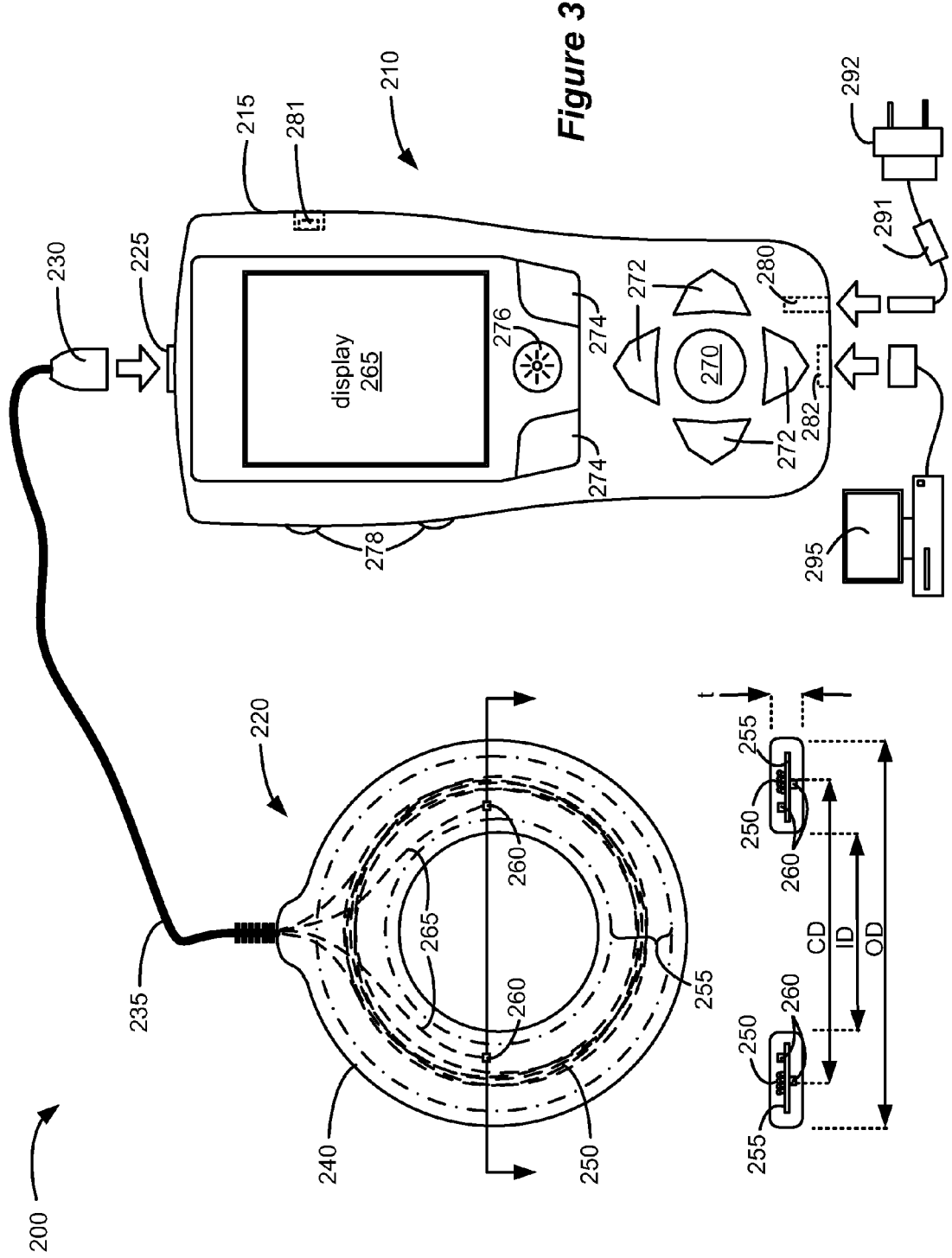
FIG. 3 shows an external controller/charger system in accordance with an embodiment of the invention comprising an external controller with a detachable external charging coil assembly.

One embodiment of an improved external controller/charger system 200 is illustrated in FIG. 3. In system 200, data telemetry and charging functionality are integrated. The system 200 comprises two main components: an external controller 210 and an external charging coil assembly 220 that is coupleable thereto. When the external charging coil assembly 220 is coupled to the external controller 210 as discussed further below, the system 200 can be used to both send and receive data telemetry to and from the IPG 100, and to send power to the IPG 100. As will be discussed further below, the external controller 210 controls data telemetry by energizing at least one coil 62a or 62b (FIG. 4) within the external controller 210, and the external controller 210 controls power transmission by energizing a charging coil 250 in the external charging coil assembly 220, which is otherwise devoid of its own control, power, and user interface.

Allowing the external charging coil assembly 220 to be attached to and detached from the external controller 210 achieves good integration of the charging and data telemetry functions in an implantable medical device system, and comprises a solution that mitigates many of the problems discussed in the Background. First, because the external charging coil assembly 220 does not contain a substantial amount of electronics, such as its own display, battery, microcontroller, etc., it is less bulky and easier to carry in conjunction with the external controller 210. Moreover, the external charging coil assembly 220 lacks its own user interface, which instead is integrated as part of the user interface of the external controller 210. This makes the system 200 easier to use, as the patient does not need to learn how to use or manipulate two completely independent devices. Because the external controller 210 powers both itself and the external charging coil assembly 220, there is only one battery to replace and/or recharge. The result is a cheaper, simpler, more compact, and more convenient data telemetry and charging solution for the patient having a medical implant.

Housing 215 of the controller 210 contains an additional port 225 into which a connector 230 on the charging coil assembly 220 can be placed. The connector 230 is connected by a cable 235 to a charging coil housing 240 portion of the assembly 220. The charging coil housing 240 contains the charging coil 250, while the external controller housing 215 contains the data telemetry coils 62a and 62b, which are disclosed in FIG. 4 and will be discussed later. In the depicted embodiment, the charging coil housing 240 is roughly donut shaped to accommodate the circular shape of the charging coil 250, but the shape can vary. For example, the charging coil housing 240 can be disc shaped and thus can lack a central hole.

The charging coil 250 is preferably comprised of Litz wire, such as 25/38 Litz wire (in which each wire contains 25 individually-insulated strands of 38 gauge wire) or 50/41 Litz wire (50 individually-insulated strands of 41 gauge wire). In a preferred implementation, the charging coil 250 exhibits an inductance of approximately 400 microhenries, which can be achieved by using approximately 75 turns of 25/38 Litz wire wound with a coil diameter (CD) of 5.5 cm. However, these values for the charging coil 250 are a matter of personal choice for the designer, and can be varied depending on the circumstances. For example, the coil diameter (CD) is preferably made large to maximize the reliability of coupling with the corresponding charging coil 18 in the IPG (see FIG. 2). However, a larger coil diameter will require more power, which will increase the draw from the battery 126 in the external controller 210. (The controller 210's battery 126 will be discussed in further detail below).

The external charging coil assembly 220 can be assembled in many different ways, and one method for forming a flexible assembly is explained in detail here. As best seen in cross-section in FIG. 3, assembly can begin with a substrate 255 for holding the electronic components, such as the charging coil 250 and temperature-sensing thermistors 260, discussed further below. The substrate 255, if used, is preferably flexible and comprises any type of flexible substrates used to carry electronic circuitry, such as Kapton or Polyimide. The charging coil 250 is wound to the specified number of turns, and is wound concurrently with the deposition of a silicone, such that the resulting coil 250 comprises wire windings in a flexible, insulative matrix of silicone.

Thereafter, thermistors 260 are placed on the substrate and attached to appropriate lead wires 265 leading towards the cable 235. As will be discussed further below, the thermistors 260 are designed to sense the temperature of the charging coil housing 240 during charging, i.e., when the charging coil 250 is energized, to ensure that a safe temperatures are maintained. For example, because the charging coil housing 240 may come into contact with a patient's skin, the thermistors 260 can report the temperature back to the external controller 210, which in turn can temporarily disable further charging if the temperature is excessive (e.g., over 41 C or approximately 106 F). Thermistors 260 however are not strictly mandatory, and further can vary in number. For example, as shown in FIG. 3, thermistors 260 can appear on the top or bottom of the substrate 255 (as shown in the cross section) or on opposing sides of the housing 240 (as shown in the planar view). If the housing 240 is disk shaped, the substrate 255 can likewise be disc shaped, and the thermistors 260 could in that arrangement be alternatively or additionally located in the middle of the housing.

Once the electrical components are mounted to the substrate 255, the lead wires are connected to wires in the cable 235. Then, the charge coil housing 240 is mold injected around the resulting substrate 255. Silicone is preferred as the fill material for the mold injection process, because it yields a charge coil housing 240 that is soft and flexible. The result is a charge coil housing 240 that is comfortable and can conform to the patient's body. This is especially important in an application where the patient must sit or otherwise place weight on the housing 240 to place it in a proper alignment with the IPG 100 while charging. The particular size of the charge coil housing 240 is not particularly important, but in one embodiment can comprise an inner diameter (ID) of 4.0 cm, an outer diameter (OD) of 7.0 cm, and a thickness (t) of 3.0 mm.

While the substrate 255 can be useful to stabilize the charging coil 250 and any associated electronics (e.g., temperature sensors 260) prior to mold injection of the silicone, a substrate 255 is not strictly required. Mold injection of the housing 240 to encapsulate these components can occur even without the benefit of a substrate 255.

The external controller 210 controller and integrates data telemetry and charging functionality via its microcontroller and software (not shown), and provides the user access to such functionality through a user interface. The user interface generally allows the user to telemeter data (such as a new therapy program) from the external controller 210 to the IPG 100, to charge the battery 26 in the IPG, or to monitor various forms of status feedback from the IPG. The user interface is somewhat similar to a cell phone or to other external controllers used in the art, in that it includes a display 265, an enter or select button 270, and menu navigation buttons 272. Soft keys 278 can be used to select various functions, which functions will vary depending on the status of the menu options available at any given time. A speaker is also included within the housing 215 to provide audio cues to the user (not shown). Alternative, a vibration motor can provide feedback for users with hearing impairments.

It is generally preferred that the keys and buttons in the user interface become automatically locked after some time period of non use (such as one minute). This allows the user to then put the external controller 210 in his pocket for example without fear that any keys or buttons will become accidentally depressed. Unlock button 281, recessed into the side of the housing, can be used to unlock the keys and buttons, and can be activated by pressing and holding that button for some duration of time (e.g., one second).

The display 265 optimally displays both text and graphics to convey necessary information to the patient such as menu options, stimulation settings, IPG battery status, external controller battery status, or to indicate if stimulation is on or off, or to indicate the status of charging.

The display 265 may comprise a monochrome liquid crystal display (LCD) using twisted nematic (TN) or super twisted nematic (STN) liquid crystal technology. The advantages of monochrome TN or STN LCDs are low cost, low power, and ease of programming. However, such benefits can be accompanied by disadvantages, such as a relatively low resolution, narrow viewing angle (typically only 60 degrees), low contrast, low brightness, and slow response times. Brightness and contrast can be improved with a backlight, but this may increase cost, power consumption, complexity, and electromagnetic interference (EMI), especially in displays 265 with electroluminescent (EL) backlights, which require special high frequency and high voltage drive circuitry. LED backlights require lower voltages and are well-suited for minimizing electrical noise.

The display 265 may also comprise a color display such as a color super twisted nematic (CSTN) or thin-film transistor (TFT) LCDs. Compared to monochrome TN or STN LCDs, color CSTN and TFT LCDs provide higher resolution, wider viewing angles, higher contrast, higher brightness, and faster response times. CSTN and TFT LCDs can range from 8-bit color displays (256 colors) to as high as 32-bit color displays (4.29 billion colors). Color LCDs are typically backlit with white light-emitting diodes (LEDs) which are low cost, low in EMI, more reliable, and simpler to implement than traditional EL backlights. CSTN and TFT LCDs can also be made such that a backlight is not needed if ambient light is sufficient. This type of transreflective LCD can be visible even in direct sunlight.

The display 265 may further comprise an organic light-emitting diode (OLED) display. OLED displays are available in monochrome, grayscale (typically 4-bit), color (usually two or three colors), or full-color (8-bit to 32-bit color). OLED displays inherently have higher contrast (typically 5000:1) and wider viewing angles (nearly 180 degrees) when compared with color LCDs. OLEDs differ from color LCDs in that OLEDs are emissive (light-emitting) instead of transmissive (light-filtering). In this regard, OLEDs emit light when a voltage is applied across an active material (e.g., an organic polymer), whereas LCDs require color filters and a white backlight to produce color. Because a separate backlight is not needed, OLED displays can be made significantly thinner than color LCDs, which in turn means that the external controller 210 can be made smaller. In addition, a typical image displayed on an OLED display requires less power than a comparable image on a color LCD. OLED displays are also potentially lower in cost than LCDs because, as mentioned, a backlight is not necessary, which can be a significant portion of the display's cost.

Figures 1A, 1B:
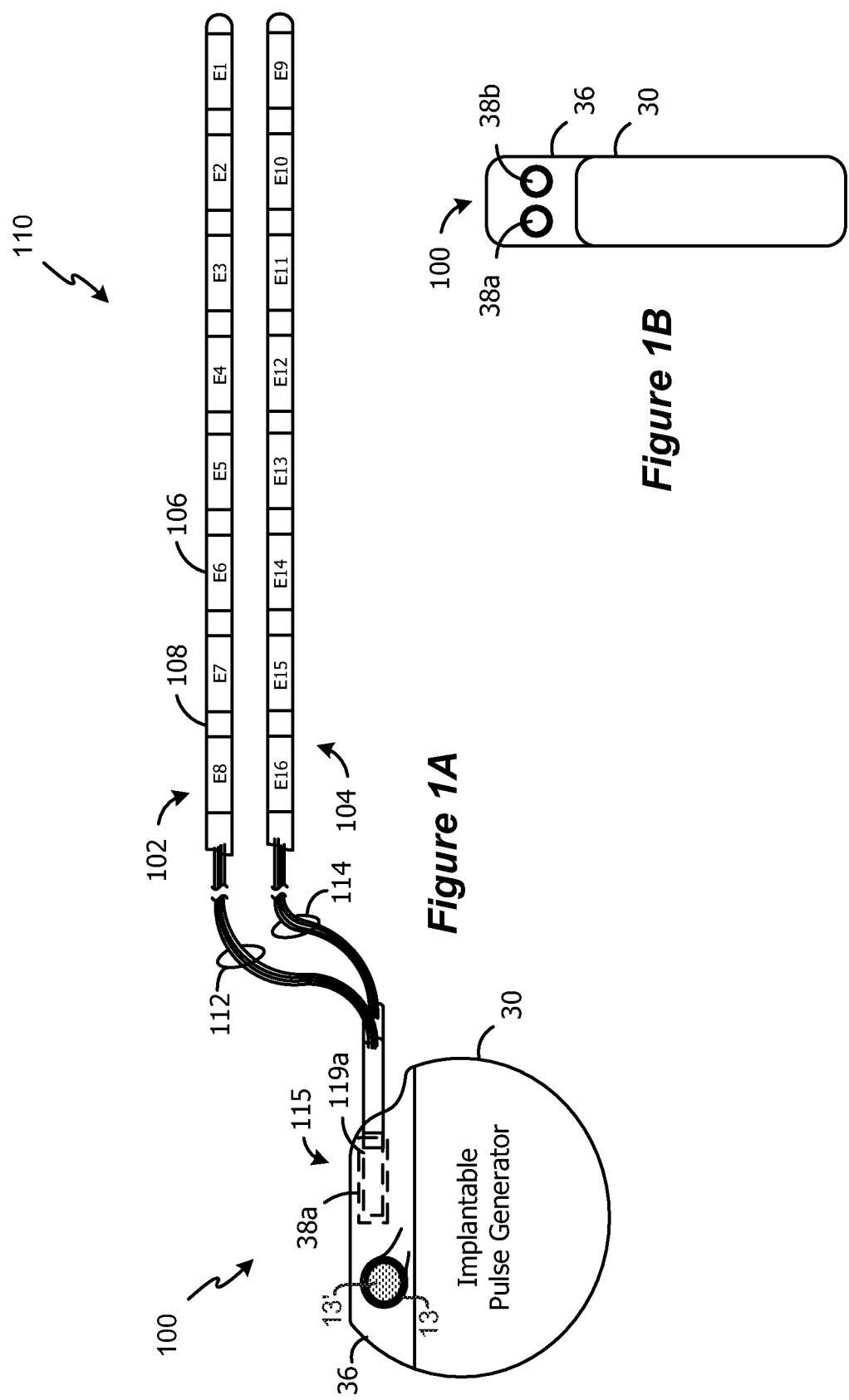
FIGS. 1A and 1B show an implantable pulse generator (IPG), and the manner in which an electrode array is coupled to the IPG in accordance with the prior art.
Figure 2:
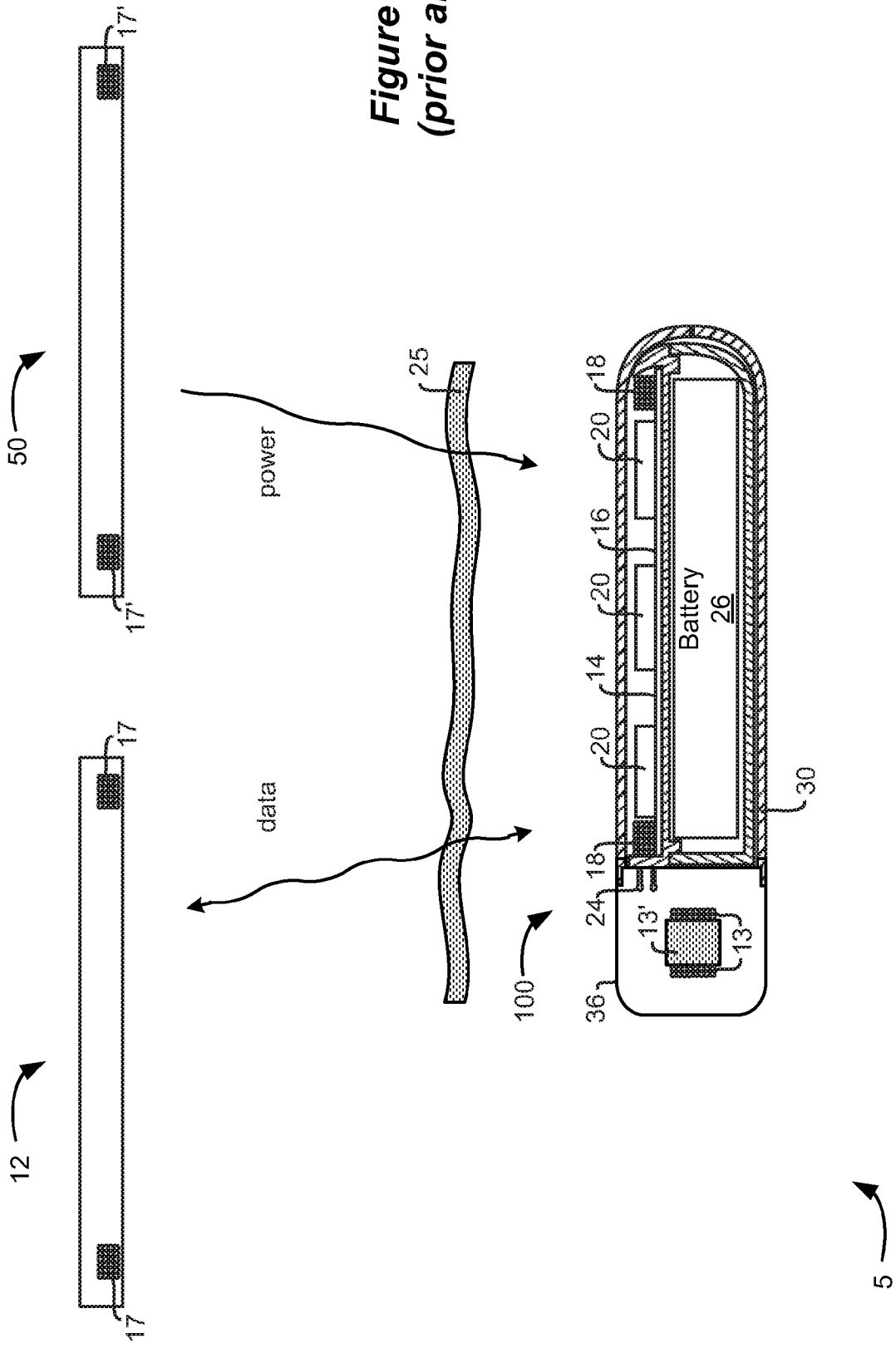
FIG. 2 shows wireless communication of data between an external controller and an IPG, and wireless transfer of power from an external charger to the IPG.
Figure 4:
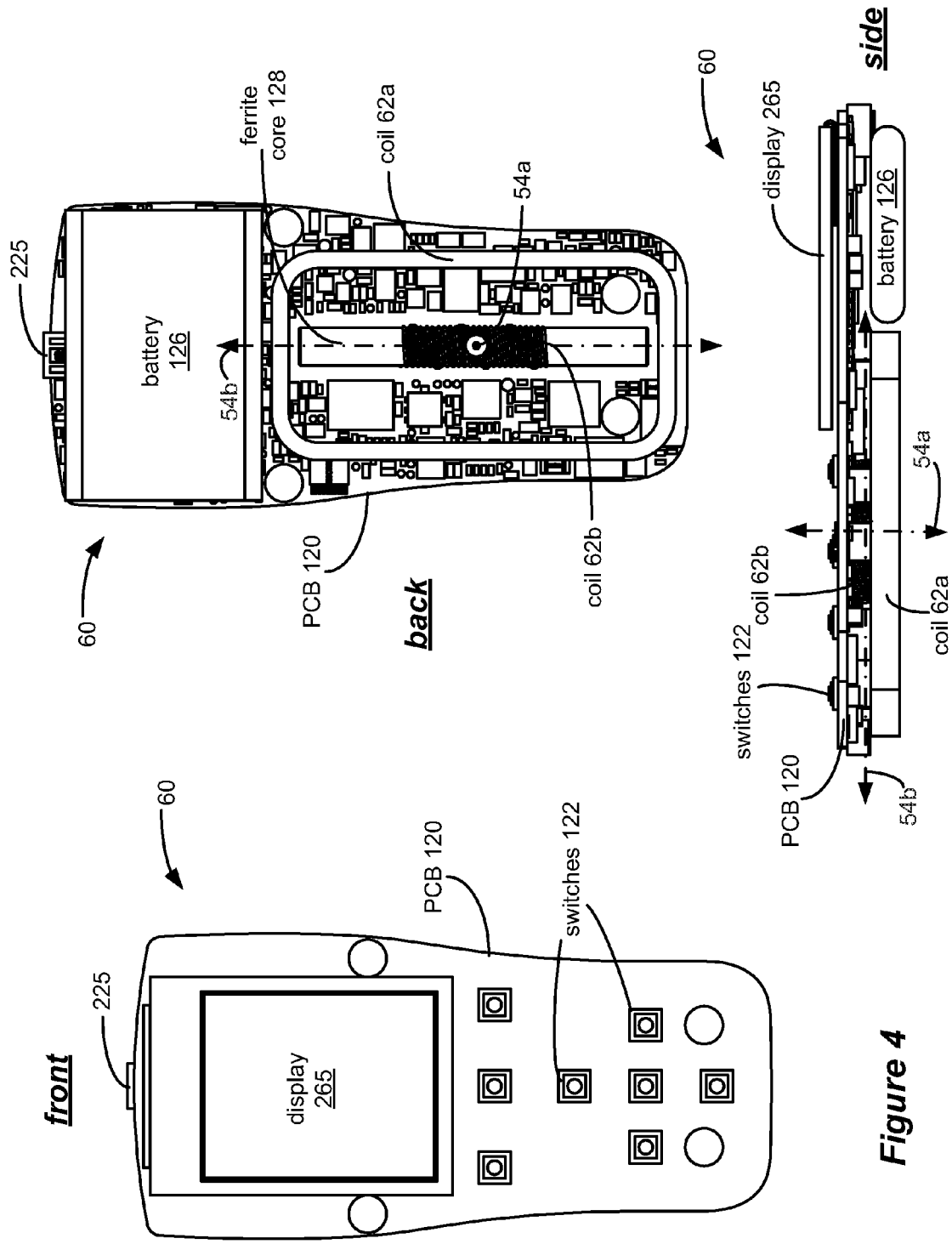
FIG. 4 shows the internal components of the external controller of FIG. 3.

The internal structure of the external controller 210, with its housing 215 removed, is shown in FIG. 4. As shown, a printed circuit board (PCB) 120 is central to the internal construction of the controller 210. The front side of the PCB 120 carries aspects of the user interface, including the display 265 and pressure-sensitive switches 122 for receiving presses to the various user interface buttons 270, 272, 274, and 276 (FIG. 3). In the depicted embodiment, the telemetry coils 62*a* and 62*b* and the battery 126, are located on the back side of the PCB 120, along with other integrated and discrete components necessary to implement the functionality of the external controller, such as the microcontroller and firmware holding the operation system software. The external controller 210 would also contain the stimulation circuitry for energizing the charging coil 250, which circuitry would be similar to that traditionally found in a discrete external charger 50 (FIG. 2).

Power to operate the external controller 210, including the power needed to energize the telemetry coils 62*a* and 62*b* and the external charging coil 250 comes from a battery 126. The battery 126 can comprise standard disposable alkaline batteries (e.g., two to four AA or AAA batteries). However, in a preferred embodiment, the battery 126 is rechargeable, which reduces battery costs and waste. In particular, a Lithium (Li)-ion battery or a Li-ion polymer battery is preferred for the battery 126. Such batteries have high cell voltages (e.g., 4.2V), such that one cell can replace numerous alkaline cells in series. Such batteries also have high energy capacity, which can be nearly twice that of alkaline cells. A rechargeable Li-ion or Li-ion polymer battery 126 thus either allows for twice the runtime of alkaline cells in the same form factor, or the same runtime with about half the package size, which enables a smaller external controller 210 design.

Use of higher capacity of Li-ion or Li-ion polymer batteries for the battery 126 also promotes the use of higher-current drain components in the external controller 210 such as the color LCD or OLED displays 265 discussed earlier, which improve patient experience by offering a more legible display. In addition, due to the lower internal series resistance of Li-ion or Li-ion polymer batteries, significantly higher current drains can be achieved, which improves functions requiring high amounts of current, such as energizing the telemetry coils 62*a*/62*b* or the charging coil 250 in the external charging coil assembly 220. When higher currents are used to energize the coils, the communication range is increased. Furthermore, Li-ion and Li-ion polymer batteries should typically remain reliable for the life of the external controller 210, which means the battery 126 can be sealed in the housing 215 of the external controller 210. In other words, no opening needs to be made on the housing to allow a user to remove the battery 126, which improves reliability, safety, and lowers manufacturing costs. Having said this, a latched battery opening can also be provided in the housing 215 of the external controller 210 even when a rechargeable battery 126 is used to allow for battery servicing if needed.

The battery 126 can be recharged much like a cellular telephone, and so can essentially be plugged into a 120V AC wall outlet. A power port 280 (FIG. 3) can receive power using an AC power source 292 (e.g., a wall plug), which is rectified to DC levels by an AC-DC adapter 291. Alternatively, the housing 215 of the external controller 210 can carry two electrodes to allow the battery 126 to be charged while sitting in a charging cradle or docking station (not shown).

In a preferred implementation, and as seen in the back and side views of FIG. 4, the two telemetry coils 62a and 62b are respectively wrapped around axes 54a and 54b which are orthogonal. More specifically, coil 62a is wrapped in a racetrack configuration around the back of the PCB 120, while coil 62b is wrapped around a ferrite core 128 and affixed to the PCB 120 by epoxy. Further discussion of the benefits of orthogonally-oriented telemetry coils 62a and 62b can be found in U.S. patent application Ser. No. 11/853,624, filed Sep. 11, 2007, which is incorporated by reference in its entirety. Briefly, when used to transmit data, the two coils 62a, 62b are driven (for example, with FSK-modulated data) out of phase, preferably at 90 degrees out of phase. This produces a magnetic field which rotates, and which reduces nulls in the coupling between the external controller 210 and the telemetry coil 13 in the IPG 100. Should dual coils 62a, 62b also receive status transmissions from the IPG 100, the two coils are used in conjunction with receiver circuitry which likewise phase shifts the received modulated data signals from each coil and presents their sum to typical demodulation circuitry. Because the details of transmission and reception using two orthogonal coils 62a and 62b are disclosed in detail in the '624 application, they are not reiterated here.

While the use of two orthogonal telemetry coils 62a and 62b is presently preferred, a more traditional single coil approach can be used for the telemetry and reception of data. For example, coil 62a can be used exclusively for data transmissions, with coil 62b dispensed with altogether. Additionally, it should be realized that an antenna or antennas, such as might be used in other forms of wireless devices, may more generically be used in place of the telemetry coil(s) 62s and/or 62b. In other words, the means for telemetry in the external controller 210 need not comprise a coil or coils per se, and coils should be understood as one type of more generic antennas which can otherwise be used.

As noted earlier, the external controller 210 controls both data telemetry and charging functions, and therefore the user interface (the display 265, the various buttons 270-276, etc.) provides access to and feedback from both of these functions. The software in the controller 210 (preferably implemented as microcode accessible by the controller 210's microcontroller) accordingly provides logical menu options to the display 265. For example, when the controller is first turned on, the display 265 may provide selectable options for the user to either program or charge the IPG 100. If the user decides to program the IPG 100, the software would provide selectable options to allow the patient options to modify therapy, such as by altering the electrodes to be stimulated, the amplitude or frequency of such stimulation, etc. If the user chooses to charge, the external controller may investigate port 225 to see if the external charging coil assembly 220 is attached. If not, a suitable message might be displayed instructing the user to so attach the assembly before proceeding further in the menu.

In a preferred embodiment, the software only provides charging-related options to the user when the external charging coil assembly 220 is attached. Thus, when the external controller 210 is first turned on, a check is made as to whether the assembly 220 is attached. If not, only programming (i.e., data telemetry) related options are provided to the user. If the external charging coil assembly 220 is attached, then the software assumes that charging is the priority task that it must perform, and hence only charging options are provided to the user, such as an invitation to the user to start charging immediately. Likewise, if the external controller 210 senses that the external charging coil assembly 220 is attached at some point after the controller has already been turned on, the user interface options are preferably changed immediately to providing charging-related selections to the user. In any event, exactly how the software is implemented vis-à-vis data telemetry and charging functionality is not particularly important to the implementation of the invention, and such software can control the user interface of the external controller 210 in many different ways depending on designer and user preference.

In a preferred embodiment, a data port 282 is provided to allow the external controller 210 to communicate with other devices such as a computer 295. Such a data port 282 is useful for example to share data with another machine, to allow the external controller 210 to receive software updates, or to allow the external programmer 210 to receive a starter therapy program from a clinician programmer. Data port 282 can be physically configured in any number of standard ways, and can be located in many different positions on the housing 240 of the external controller. Moreover, data port 282 can be configured as dictated by any number of communication protocols, such as RS323 protocol. In one advantageous implementation, data port 282 comprises an infrared port capable of wireless communication in accordance with the IRDA (Infrared Data Association) protocol. This type of port is useful because it is electrically and mechanically sealed, which reduces the possibility of potential electrical shock to the user.

Figure 5:
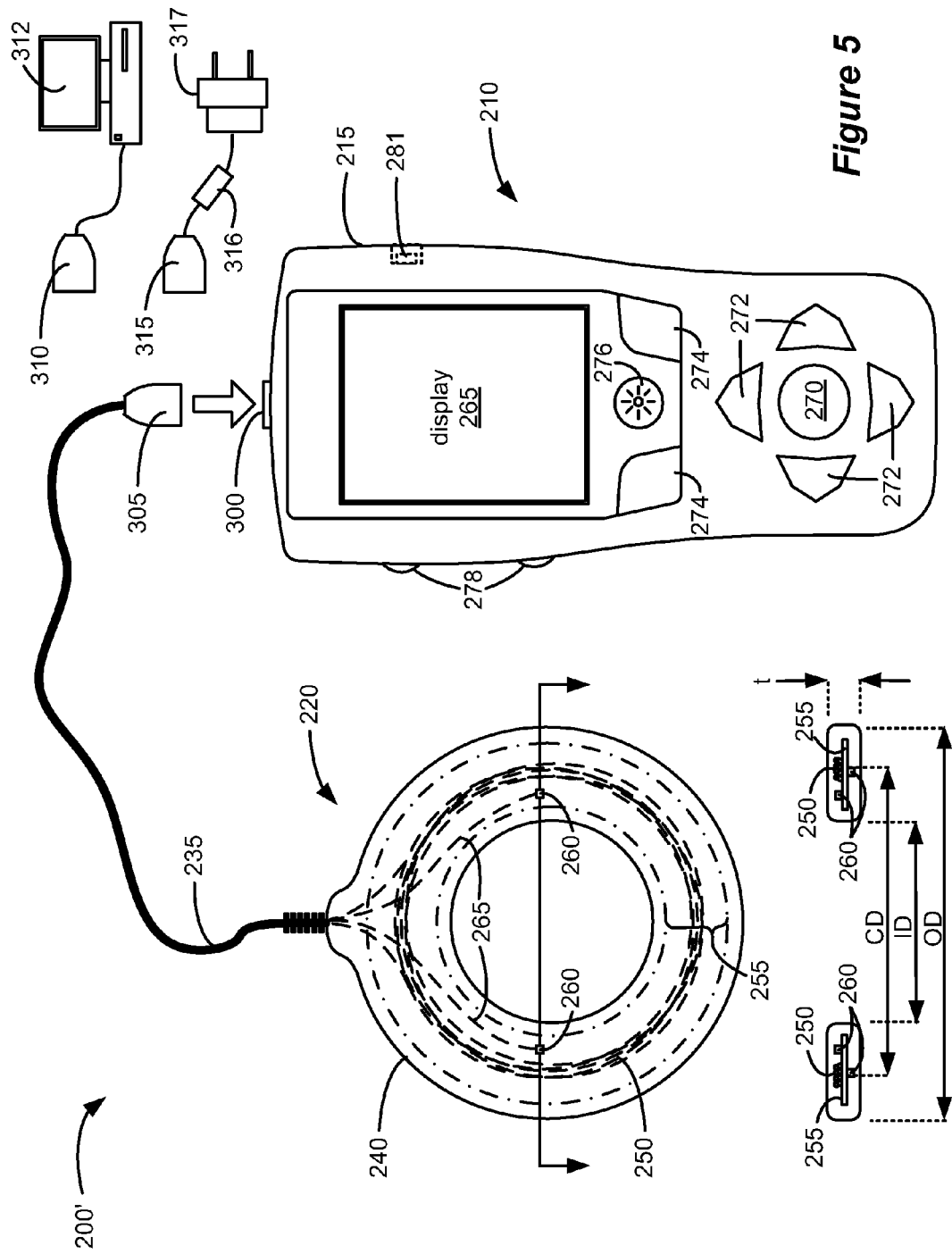
FIG. 5 shows another embodiment of an external controller/charger system in which the external controller comprises a single power, data, and external charging coil assembly port.

Another embodiment of the improved external controller/charger system 200' is illustrated in FIG. 5. This embodiment is otherwise similar to system 200 discussed earlier, except as concerns the various ports on the housing 215 of the external controller 210. In this system 200' the power, data, and external charging coil assembly ports 280, 282, and 225 (see FIG. 3) have been replaced by a single USB port 300. The USB port 300 can comprise any USB receptacle profile, such as a micro USB plug receptacle, a mini USB plug receptacle, an A-type plug receptacle, or a B-type plug receptacle.

When a USB port 300 is used, the external controller 210 can be coupled to the external charging coil assembly 305 by a matching USB connector 305. Additionally, and beneficially, this same port 300 can connect with other devices, such as a computer 312 via a USB connector 310, or a AC power source 317 via a USB connector 315 and an AC-DC adapter 316. Therefore, using the same port 300 as that used to connect the external charging coil assembly 220, the external controller 210 can be coupled to a power source and to a data source. For example, because USB protocols call for provision of DC power, either the computer 312 or the power source 317 may be used to provide power to the external controller 210, or more importantly to recharge its battery 126. Moreover, the computer 312 can be used to download programs to the external controller 210 via the USB port, or to receive status data from the external controller 210 as already explained.

Integration of the power, data, and external charging coil assembly ports into a single USB port 300 benefits the design of the system 200. First, the mechanical design of the external controller 210 is made simpler, as only a single port need be provided for. Second, the design of the external controller is safer and more reliable: having only a single port lessens the chance for unwanted moisture or electrical ingress inside of the housing of the controller 215, which might cause damage or shock.

Because there is only a single port 300, communications must be shared. For example, if when the external charging coil assembly 220 is attached, neither the computer 312 nor power source 317 can be attached. But this is not a problem, because data transfer external to the external controller 210 and/or recharging of the external controller's battery 126 should not be critical during a session in which a patient is recharging the battery 26 in his IPG 100. In fact, safety results from the inability to couple the external charging coil assembly 220 and the power source 317 at the same time, which means that no direct connection to AC power is possible while the patient is charging. This prevents a potentially hazardous situation if the transformer 316 proves to be defective.

As USB is dictated by its own communication protocol, it is a routine matter for designers to implement communications, and such details do not require repeating here. Although use of a USB port 300 and accompanying USB protocol is preferred, any other type of standardized port and protocol could be used to integrate the power, data, and external charging coil functions described herein.

Although particular embodiments of the present invention have been shown and described, it should be understood that the above discussion is not intended to limit the present invention to these embodiments. It will be obvious to those skilled in the art that various changes and modifications may be made without departing from the spirit and scope of the present invention. Thus, the present invention is intended to cover alternatives, modifications, and equivalents that may fall within the spirit and scope of the present invention as defined by the claims.

What is claimed is:

1. A system for communicating with an implantable medical device, comprising:
    an external controller integrated within a single housing, the external controller comprising two telemetry coils each wound around axes that are orthogonal within the housing for communicating data with the implantable medical device via magnetic inductive coupling; and
    an external charging coil assembly containing a charging coil for providing power to the implantable medical device, wherein the assembly is attachable to and detachable from the external controller at a port on the external controller.

2. The system of claim 1, wherein the external charging coil assembly is flexible.

3. The system of claim 1, wherein the external charging coil assembly does not contain a user interface.

4. The system of claim 1, wherein the external controller contains circuitry for energizing the charging coil.

5. The system of claim 1, wherein the port comprises a USB port.

6. The system of claim 1, wherein the external controller controls the charging coil.

7. The system of claim 1, wherein the external controller comprises a color display.

8. The system of claim 1, wherein external charging coil assembly further comprises at least one temperature sensor for reporting at least one temperature to the external controller.

* * * * *

UNITED STATES PATENT AND TRADEMARK OFFICE
CERTIFICATE OF CORRECTION

| | | |
|---|---|---|
| PATENT NO. | : 8,498,716 B2 | Page 1 of 1 |
| APPLICATION NO. | : 11/935111 | |
| DATED | : July 30, 2013 | |
| INVENTOR(S) | : Chen et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1121 days.

Signed and Sealed this

Thirteenth Day of January, 2015

Michelle K. Lee
*Deputy Director of the United States Patent and Trademark Office*